US006649175B1

(12) United States Patent
Haslwanter et al.

(10) Patent No.: US 6,649,175 B1
(45) Date of Patent: Nov. 18, 2003

(54) SKIN BARRIER COMPOSITION

(75) Inventors: Joseph A. Haslwanter, Germantown, TN (US); William F. Rencher, Ashburn, VA (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 447 days.

(21) Appl. No.: 09/303,413

(22) Filed: May 3, 1999

Related U.S. Application Data

(60) Provisional application No. 60/084,181, filed on May 4, 1998.
(51) Int. Cl.$^7$ .............................. A61K 6/00; A61K 7/00; A61K 27/00; A01N 31/01; A01N 25/00
(52) U.S. Cl. ........................ 424/401; 514/762; 514/865; 514/943
(58) Field of Search ................................. 424/400, 401; 514/865, 943, 762

(56) References Cited

U.S. PATENT DOCUMENTS 5,378,468 A * 1/1995 Suffis et al.
5,443,855 A * 8/1995 Wolf et al.

* cited by examiner

*Primary Examiner*—Sreeni Padmanabhan
*Assistant Examiner*—Lauren Q. Wells
(74) *Attorney, Agent, or Firm*—Robert A. Franks

(57) ABSTRACT

A skin barrier lotion for protection against contact with irritants comprises: about 5 to 15 percent by weight of a long-chain fatty acid; about 1 to 5 percent by weight of a long-chain fatty alcohol; about 1 to 10 percent by weight of a hydrocarbon oil; about 1 to 30 percent by weight of a silicone skin protectant; about 0.5 to about 5 percent by weight of an alkanolamine; about 0.5 to about 5 percent by weight of a humectant; about 0.5 to about 10 percent by weight of an inorganic skin protectant; about 0.5 to 15 weight percent of a preservative; and about 50 to 90 percent by weight water. Optionally, the lotion will also contain up to about 5 percent by weight of a fragrance, odor neutralizer or a mixture thereof.

27 Claims, No Drawings

US 6,649,175 B1

SKIN BARRIER COMPOSITION

CROSS-REFERENCE TO RELATED APPLICATION

This application claims the benefits under 35 U.S.C. §119(e) from provisional application Ser. No. 60/084,181 filed on May 4, 1998.

INTRODUCTION TO THE INVENTION

The present invention pertains to compositions which protect the skin against the effects of irritants, and more particularly to compositions which can be applied to the skin for protection against contact with body fluids and wastes.

A substantial fraction of the population suffers at some time from a form of incontinence. Incontinence is normal with infants, but frequently incontinence is also the result of aging or some other uncontrolled mental or physiologic process. Absorptive pads and impervious garment liners are available to contain the excreted wastes and prevent their leakage onto clothing, furniture and the like, but many of these tend to maintain the wastes in contact with skin for prolonged periods and cause dermatolologic problems.

The skin normally is capable of maintaining adequate internal moisture to remain pliable. This condition typically requires an internal relative humidity ("RH") at least about 60 percent. Various factors, including the presence of lipid components in the skin, work to maintain proper RH values for most aspects of normal living. However, exposure to external moisture sources can cause a depletion of skin lipids and a consequential dermatitis. This condition is aggravated when the external moisture source also contains irritating chemicals, such as are present in body wastes.

The are commercially available products for coating the skin to prevent deleterious contact with chemical substances. Such products are generally called "barrier" creams, lotions or ointments and are based on impervious substances such as petrolatum, silicone greases, heavy oils, waxes and the like. Unfortunately, these materials leave a very greasy, sticky or oily uncomfortable coating on the skin and therefore are best suited as substitutes for vinyl or rubber gloves, applied just prior to exposure to detergents, industrial chemicals, etc. For application to the pubic and perianal regions of the body, many persons would prefer a substance similar to those lotions, creams and the like normally used for the typical non-barrier skin care products; these are commonly emulsions of the oil-in-water type, since the skin absorbs these formulations more readily than it does oil-external formulations and does not acquire a greasy or oily feel after application of the product.

Accordingly, it was undertaken by the present inventors to develop an oil-in-water barrier lotion formulation which, after application to the skin, promptly feels dry, smooth and non-oily, and which effectively inhibits skin irritation from prolonged contact with body wastes or other irritants.

SUMMARY OF THE INVENTION

The invention resides in a barrier lotion comprising: about 5 to 15 percent by weight of a long-chain fatty acid; about 1 to 5 percent by weight of a long-chain fatty alcohol; about 1 to 10 percent by weight of a hydrocarbon oil; about 1 to 30 percent by weight of a silicone skin protectant; about 0.5 to about 5 percent by weight of an alkanolamine; about 0.5 to about 5 percent by weight of a humectant; about 0.5 to about 10 percent by weight of an inorganic skin protectant; about 0.5 to 15 weight percent of a preservative; and about 50 to 90 percent by weight water. A very desirable additional component is up to about 5 percent by weight of a fragrance, odor neutralizer or a mixture thereof.

DETAILED DESCRIPTION OF THE INVENTION

Throughout this specification, the term "percent" is intended to mean, unless the context clearly indicates otherwise, percentages by weight. Various formulation components are identified herein by their adopted names as given by J. M. Nikitakis et al., Eds., CTFA *International Cosmetic Ingredient Dictionary*, Fourth Ed., The Cosmetic, Toiletry and Fragrance Association, Washington, D.C., 1991. The functions performed by various components are listed by J. A. Wenninger et al., Eds., CTFA *Cosmetic Ingredient Handbook*, Second Ed., The Cosmetic, Toiletry and Fragrance Association, Washington, D.C., 1992.

The invention encompasses skin barrier lotions comprising: about 5 to 15 percent by weight of a long-chain fatty acid; about 1 to 5 percent by weight of a long-chain fatty alcohol; about 1 to 10 percent by weight of a hydrocarbon oil; about 1 to 30 percent by weight of a silicone skin protectant; about 0.5 to about 5 percent by weight of an alkanolamine; about 0.5 to about 5 percent by weight of a humectant; about 0.5 to about 10 percent by weight of an inorganic skin protectant; about 0.5 to 15 weight percent of a preservative; and about 50 to 90 percent by weight water. Optionally, there also is included up to about 5 weight percent of a fragrance odor "neutralizer" or mixtures thereof.

The long-chain fatty acid is generally a substituted or unsubstituted carboxylic acid, having carbon atoms (inclusive of the carboxy group) numbering about 12 to about 22. Of course, the acid must be chosen from those which are safe for prolonged skin contact when formulated in water-external emulsions according to the general teachings herein. The acids generally should have melting points higher than the temperature of the skin to which the barrier lotion is applied, so that the acid will be at least partially in solid form after application to the skin; the solid phase permits the acid to give a "dry" feel to the skin and facilitates the occlusive function of the acid. Preferred normal carboxylic acids for purposes of the invention include, without limitation, lauric acid, myristic acid, palmitic acid, stearic acid, arachidic acid and tricosanoic acid. In general, the unsaturated acids will have melting points too low to be preferred for this invention. Concentrations of the acid are generally about 5 to 15 percent, preferably about 8 to 11 percent.

The inventors presently have a preference for stearic acid, particularly in the "triple pressed" purity grade to obtain a product having consistent properties.

An alkanolamine component is desired, as this material can react with the long chain fatty acid to form an emulsifier of the type frequently used to produce cosmetic skin creams and lotions. Several alkanolamines can be used, including ethanolamine, diethanolamine, triethanolamine, isopropanolamine, diisopropanolamine, triisopropanolamine, methylethanolamine and others. About 0.5 to 5 percent alkanolamine will be present in the formulation, preferably about 1 to 2 percent. The long chain fatty acid content should be adjusted, such that an excess of fatty acid is present over that amount which will completely react with the alkanolamine to form a salt; sufficient excess acid should be used to produce a formulation having pH values approximating that of the skin, i.e., averaging about 5 to 6. Particularly when the long chain fatty acid is stearic acid, the choice of triethanolamine is preferred, as the emulsifier salt formed from these components gives a very desirable lotion product in accordance with the invention.

A further required component is the long chain fatty alcohol, being branched or unbranched, substituted or unsubstituted, and having about 14 to about 22 carbon atoms. This component also provides an occlusive effect and, for obtaining the desired "dry" feel on the skin, should have a melting point higher than the temperature of the skin. Preferred normal alcohols include myristyl alcohol, cetyl alcohol and stearyl alcohol. The alcohol component is typically present in a barrier lotion at concentrations of about 1 to about 5 percent, and more preferably about 1 to about 4 percent.

A hydrocarbon oil or plant- or animal-derived oil is included in a formulation as a skin conditioning agent to maintain an appropriate moisture level within the skin, and may act as a humectant to assist in controlling the rate of water loss from the emulsion film as it is being applied. Mineral oil has been found preferable for this purpose, and is generally present at about 1 to about 10 percent. Preferred concentrations are about 0.5 to about 5 percent. The amount of this component should be minimized, to prevent an oily feel on the skin and to facilitate removal of the film, when desired. Mineral oils are available in a wide range of specific gravity and viscosity specifications, most of which are suitable for use in the invention; however, users generally prefer the skin feel of compositions having the lower specific gravities and viscosities.

Other humectants, such as glycerol, ethylene or propylene glycols, sorbitol, mannitol and other hygroscopic substances will be included, as necessary to inhibit moisture loss from the formulation as it is being applied. Without sufficient humectant, the insoluble solids (e.g., stearic acid and cetyl alcohol) tend to not spread evenly as the emulsion breaks down from evaporative water losses; this results in aggregation of the insoluble solids, which adversely affects the appearance and sensory quality of the film. The humectant will normally be present in amounts about 0.5 to about 5 percent, preferably about 1 to about 2 percent of the formulation.

The silicone skin protectant component is included at levels about 1 to 30 percent, preferably about 4 to 10 percent, for its barrier properties. However, all barrier ingredients will cause an oily or greasy sensation on the skin, with the very impervious petrolatums probably giving the most unpleasant feel. Using a silicone material, such as amodimethicone, cyclomethicone, hexadecyl methicone, dimethicone, methicone, vinyidimethicone and the like minimizes the oily sensation, which can be even further reduced by incorporating an effective amount of an inorganic skin protectant such as calamine, kaolin, zinc oxide, zinc carbonate and the like. The inorganic skin protectant will be present in the formulation at about 0.5 to about 10 percent, preferably about 0.5 to about 3 percent.

Skin care emulsions usually contain a preservative, to prevent microbial proliferation during storage and use of the product. This effect is particularly important for the product of this invention, which during use may be in contact with fluids having a significant microbial content. It is therefore desirable to incorporate an excess of preservative, over that needed solely for product storage stability; generally about 0.5 to about 15 percent preservative will be included, preferably about 0.5 to about 5 percent. Preservatives from at least the following chemical classes are suitable for use in the invention: phenols, alcohols, aldehydes, dyes, surfactants, furan derivatives, quinoline and isoquinoline derivatives, guanidines and amidines. Among the suitable preservatives specifically considered useful are benzyl alcohol (preferred, due to its local anesthetic effect on the skin), DM DM hydantoin, imidazolidinyl urea, phenylethyl alcohol, benzalkonium chloride, and Quaternium-15.

The barrier lotion will also contain water, in amounts about 50 to about 90 percent. Such high water contents creates a "vanishing" sensation, i.e., it feels as though substantially all of the lotion is being incorporated into the skin during application. To achieve consistent formulation characteristics, it is preferable to use purified water, such as that which has been treated by deionization or reverse osmosis to remove dissolved solids.

An optional, but highly desirable, component is a fragrance or odor neutralizer. This is of readily apparent importance when the lotion is used under an absorptive pad or other incontinence device. Many of the pleasant fragrances commonly used in skin care products are suitable, and these may be present alone or in combination with an odor neutralizer or absorber. Odor neutralizers and absorbers are also useful as an alternative to a fragrance. The inventors have found that the proprietary deodorizer ORDENONE™ sold by Belle-Aire Fragrances, Inc., Mundelein, Ill. U.S.A. is particularly effective for reducing the odors associated with incontinence. ORDENONE is described in the supplier's literature as having a semi-rigid concave molecular structure which selectively captures malodorous volatile mercaptan, sulfide, amine and other compounds, but does not affect the customary fragrance additives. In general, up to about 5 percent fragrance or odor reducer, or a combination thereof, will be used in the lotion, preferably up to about 1 percent.

Barrier lotions prepared according to the invention have the following beneficial properties:

(a) a lack of irritation potential, even for previously irritated skin;

(b) a "vanishing" sensation when applied to skin;

(c) a pearlescent appearance before being rubbed into the skin, which facilitates even applications;

(d) a "dry" feel, which becomes non-greasy a few seconds after rubbing into the skin;

(e) excellent barrier characteristics to water and body wastes;

(f) prompt removal with soap and water; and (g) excellent physical stability.

The invention will be further described by means of the following example, which is not intended to limit the scope of the appended claims in any manner.

EXAMPLE

A kilogram batch of a skin barrier lotion is prepared using the following components:

| Component | Grams |
| --- | --- |
| Part A | |
| Stearic acid | 97.5 |
| Cetyl alcohol | 24.375 |
| Light mineral oil, NF | 20 |
| Dimethicone | 60 |

-continued

| Component | Grams |
|---|---|
| Part B | |
| Water | 724.625 |
| Zinc oxide | 10 |
| Glycerol | 15 |
| Part C | |
| Water | 15 |
| Triethanolamine | 15 |
| Part D | |
| Benzyl alcohol | 10 |
| Lemon fragrance | 0.5 |
| Part E | |
| Odor neutralizer | 8 |

The lotion is prepared by the steps of: (1) combining the Part A ingredients in a suitable vessel and heating the mixture, with stirring, to about 70–75° C. to form a smooth liquid; (2) continuing the mixing and maintaining the temperature as the Part B ingredients are added, to form a uniform dispersion; (3) recirculating about 2 percent of the vessel contents per minute through an in-line motionless mixer* and back into the original vessel for a period of about 30–45 minutes while maintaining the temperature; (4) mixing together the Part C ingredients, to form a clear solution; (5) slowly adding the step 4 solution to the step 3 dispersion, while maintaining the stirring, recirculation and temperature; (6) with continued mixing, allowing the dispersion to cool to ambient temperature, adding the Part D ingredients as the temperature passes through about 402C and adding the Part E ingredient as the temperature passes through about 30–35° C.; and (7) operating the recirculation through the in-line mixer for 20–25 minutes after all ingredients have been added, as the product continues to cool.

* The mixer has mixing elements, each having four holes at oblique angles, disposed within a conduit such that a tetrahedral chamber is formed between the elements.

What is claimed is:

1. A skin barrier lotion comprising: about 5 to 15 percent by weight of a long-chain fatty acid; about 1 to 5 percent by weight of a long-chain fatty alcohol; about 1 to 10 percent by weight of an oil; about 1 to 30 percent by weight of a silicone skin protectant; about 0.5 to about 5 percent by weight of an alkanolarhine; about 0.5 to about 5 percent by weight of a humectant; about 0.5 to about 10 percent by weight of an inorganic skin protectant; about 0.5 to 15 weight percent of a preservative; and about 50 to 90 percent by weight water.

2. The lotion of claim 1, further comprising up to about 5 percent by weight of a fragrance, odor neutralizer or a mixture thereof.

3. The lotion of claim 1, wherein the fatty acid is a substituted or unsubstituted saturated carboxylic acid having about 12 to 22 carbon atoms.

4. The lotion of claim 1, wherein the fatty acid is selected from the group consisting of lauric acid, myristic acid, palmitic acid, stearic acid, arachidic acid and tricosanoic acid.

5. The lotion of claim 1, wherein the fatty acid comprises stearic acid.

6. The lotion of claim 1, wherein the long chain fatty alcohol has about 14 to 22 carbon atoms.

7. The lotion of claim 1, wherein the long chain fatty alcohol is selected from the group consisting of myristyl alcohol, cetyl alcohol and stearyl alcohol.

8. The lotion of claim 1, wherein the long chain fatty alcohol comprises cetyl alcohol.

9. The lotion of claim 1, wherein the oil is selected from the group consisting of mineral oils, plant-derived oils and animal-derived oils.

10. The lotion of claim 1, wherein the oil comprises a light mineral oil.

11. The lotion of claim 1, wherein the silicone skin protectant is selected from the group consisting of as amodimethicone, cyclomethicone, hexadecyl methicone, dimethicone, methicone and vinyldimethicone.

12. The lotion of claim 1, wherein the silicone skin protectant comprises dimethicone.

13. The lotion of claim 1, wherein the alkanolamine is selected from the group consisting of ethanolamine, diethanolamine, triethanolamine, isopropanolamine, diisopropanolamine, triisopropanolamine and methylethanolamine.

14. The lotion of claim 1, wherein the alkanolamine comprises triethanolamine.

15. The lotion of claim 1, wherein the humectant is selected from the group consisting of glycerol, ethylene glycol, propylene glycol, sorbitol and mannitol.

16. The lotion of claim 1, wherein the humectant comprises glycerol.

17. The lotion of claim 1, wherein the inorganic skin protectant is selected from the group consisting of calamine, kaolin, zinc oxide and zinc carbonate.

18. The lotion of claim 1, wherein the inorganic skin protectant comprises zinc oxide.

19. The lotion of claim 1, wherein the preservative is selected from the group consisting of phenols, alcohols, aldehydes, dyes, surfactants, furans, quinolines and isoquinolines, guanidines and amidines.

20. The lotion of claim 1, wherein the preservative comprises an alcohol.

21. The lotion of claim 1, wherein the preservative comprises benzyl alcohol.

22. The lotion of claim 1, wherein the long chain fatty acid is present in stoichiometric excess over that amount needed to form a salt with the alkanolamine.

23. The lotion of claim 22, wherein the long chain fatty acid is present in amounts which produce lotion pH values about 5 to 6.

24. A skin barrier lotion comprising: about 8 to 11 percent by weight of a long-chain fatty acid; about 1 to 4 percent by weight of a long-chain fatty alcohol; about 0.5 to 5 percent by weight of an oil; about 4 to 8 percent by weight of a silicone skin protectant; about 1 to about 2 percent by weight of an alkanolamine; about 1 to about 2 percent by weight of a humectant; about 0.5 to about 3 percent by weight of an inorganic skin protectant; about 0.5 to 5 weight percent of a preservative; and about 50 to 90 percent by weight water.

25. The lotion of claim 24, further comprising up to about 1 percent by weight of a fragrance, odor neutralizer or a mixture thereof.

26. A skin barrier lotion comprising: about 8 to 11 percent by weight of stearic acid; about 1 to 4 percent by weight of cetyl alcohol; about 0.5 to 5 percent by weight of a light mineral oil; about 4 to 8 percent by weight of dimethicone; about 1 to about 2 percent by weight of triethanolamine; about 1 to about 2 percent by weight of glycerol; about 0.5 to about 3 percent by weight of zinc oxide; about 0.5 to 5 weight percent of benzyl alcohol; and about 50 to 90 percent by weight water.

27. The lotion of claim 26, further comprising up to about 1 percent by weight of a fragrance, odor neutralizer or a mixture thereof.

* * * * *